United States Patent
Ishii et al.

(10) Patent No.: US 12,216,106 B2
(45) Date of Patent: Feb. 4, 2025

(54) STORAGE HYDROGEN AMOUNT ESTIMATION METHOD AND DEVICE

(71) Applicant: Nippon Telegraph and Telephone Corporation, Tokyo (JP)

(72) Inventors: Ryuta Ishii, Musashino (JP); Takuya Kamisho, Musashino (JP); Norihiro Fujimoto, Musashino (JP); Masayuki Tsuda, Musashino (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 238 days.

(21) Appl. No.: 17/780,308

(22) PCT Filed: Dec. 3, 2019

(86) PCT No.: PCT/JP2019/047202
§ 371 (c)(1),
(2) Date: May 26, 2022

(87) PCT Pub. No.: WO2021/111518
PCT Pub. Date: Jun. 10, 2021

(65) Prior Publication Data
US 2022/0412941 A1    Dec. 29, 2022

(51) Int. Cl.
*G01N 33/2025* (2019.01)
*G01N 17/00* (2006.01)

(52) U.S. Cl.
CPC ....... *G01N 33/2025* (2019.01); *G01N 17/006* (2013.01)

(58) Field of Classification Search
CPC .................................................. G01N 33/2025
USPC .............................................................. 73/86
See application file for complete search history.

(56) References Cited

FOREIGN PATENT DOCUMENTS

| JP | 2018-200292 A | 12/2018 | |
| JP | 2019-100939 A | 6/2019 | |
| WO | WO-2017013751 A1 * | 1/2017 | .............. H02J 15/00 |

OTHER PUBLICATIONS

Fujimoto et al. Machine translation of WO 2017013751 A1. Published Jan. 2017. Accessed Mar. 2024. (Year: 2017).*

(Continued)

*Primary Examiner* — Walter L Lindsay, Jr.
*Assistant Examiner* — Philip T Fadul
(74) *Attorney, Agent, or Firm* — Workman Nydegger

(57) ABSTRACT

An occluded hydrogen content estimation method implemented by an occluded hydrogen content estimation device performs an occluded hydrogen content estimation step in which, based on an occluded hydrogen unit content which is a content of hydrogen occluded in a metal due to a change in humidity from a wet state to a dry state, a period after the metal is placed, and meteorological data corresponding to the period for an area where the metal is located, a content of occluded hydrogen that is absorbed in the metal for the period after the metal is placed is estimated. In the occluded hydrogen content estimation step, the occluded hydrogen content is estimated by multiplying the number of rainfalls in the meteorological data by the occluded hydrogen unit content.

3 Claims, 5 Drawing Sheets

(56) References Cited

OTHER PUBLICATIONS

Takai et al. "Hydrogen in trapping states innocuous to environmental degradation of high-strength steels." ISIJ international 43.4 (2003): 520-526. (Year: 2003).*

Tooru Tsuru, *Electrochemical Measurements for Hydrogen Entry and Permeation of Steel,* Materials and Environment, vol. 63, No. 1, 2014, pp. 3-9.

* cited by examiner

| DATE | MINATO-KU |
|---|---|
|  | TOTAL AMOUNT OF RAINFALL (mm) |
| January 1st, 2019 | 0.0 |
| January 2nd, 2019 | 0.0 |
| January 3rd, 2019 | 0.0 |
| January 4th, 2019 | 0.0 |
| January 5th, 2019 | 0.5 |
| January 6th, 2019 | 0.0 |
| January 7th, 2019 | 0.0 |
| January 8th, 2019 | 12.5 |

⋮    ⋮

STORAGE HYDROGEN AMOUNT ESTIMATION METHOD AND DEVICE

TECHNICAL FIELD

The present invention relates to an occluded hydrogen content estimation method for estimating a content of hydrogen generated due to corrosion that is absorbed and stored in a metal, and a device therefor.

BACKGROUND ART

Metal structures located outdoors, such as infrastructure facilities, are corroded through exposure to the wind and rain. Hydrogen generated by corrosion reactions is absorbed in a metal and causes brittle fracture (hydrogen embrittlement).

The higher hydrogen content in the metal increases the probability of fracture. Therefore, it is important to estimate the hydrogen content in the metal. A method for measuring a hydrogen content in a metal includes, for example, a thermal desorption analyzer (TDA) and a hydrogen permeation test (Non-Patent Literature 1). The methods disclosed in Patent Literatures 1 and 2 and the like are also known.

CITATION LIST

Patent Literature

Patent Literature 1: Japanese Patent Laid-Open No. 2019-100939
Patent Literature 2: Japanese Patent Laid-Open No. 2018-200292

Non-Patent Literature

Non-Patent Literature 1: Tooru Tsuru, "Electrochemical Measurements for Hydrogen Entry and Permeation of Steel", Zairyo-to-Kankyo, 63, 3-9 (2014)

SUMMARY OF THE INVENTION

Technical Problem

For example, the thermal desorption analyzer has a sample space, which is so small that only a small sample can be measured. Therefore, the metal structure needs to be destroyed and processed before measurement of the occluded hydrogen content. Further, in the hydrogen permeation test, processing is required to plate one side of a sample to attach an electrode thereto.

As described above, the conventional occluded hydrogen content estimation methods require processing of the metallic material. A problem is that in the processing, hydrogen desorbs from the metallic material and the correct hydrogen content cannot be measured.

An object of the present invention, which has been made in consideration of the above problem, is to provide an occluded hydrogen content estimation method that allows determination of an occluded hydrogen content in a metal structure in a non-destructive/non-processing manner, and a device therefor.

Means for Solving the Problem

An occluded hydrogen content estimation method according to an aspect of the present invention is an occluded hydrogen content estimation method implemented by an occluded hydrogen content estimation device. The occluded hydrogen content estimation method essentially performs an occluded hydrogen content estimation step in which, based on an occluded hydrogen unit content which is a content of hydrogen occluded in a metal due to a change in humidity from a wet state to a dry state, a period after the metal is placed, and meteorological data corresponding to the period for an area where the metal is located, a content of occluded hydrogen that is absorbed in the metal for the period is estimated.

An occluded hydrogen content estimation device according to an aspect of the present invention is an occluded hydrogen content estimation device that implements the above-mentioned occluded hydrogen content estimation direction. The occluded hydrogen content estimation device essentially includes an occluded hydrogen content estimation unit that estimates, based on an occluded hydrogen unit content which is a content of hydrogen occluded in a metal due to a change in humidity from a wet state to a dry state, a period after the metal is placed, and meteorological data corresponding to the period for an area where the metal is located, a content of occluded hydrogen that is absorbed in the metal for the period.

Effects of the Invention

According to the present invention, the occluded hydrogen content in the metal structure can be estimated in a non-destructive/non-processing manner.

DESCRIPTION OF EMBODIMENTS

Figure 1:
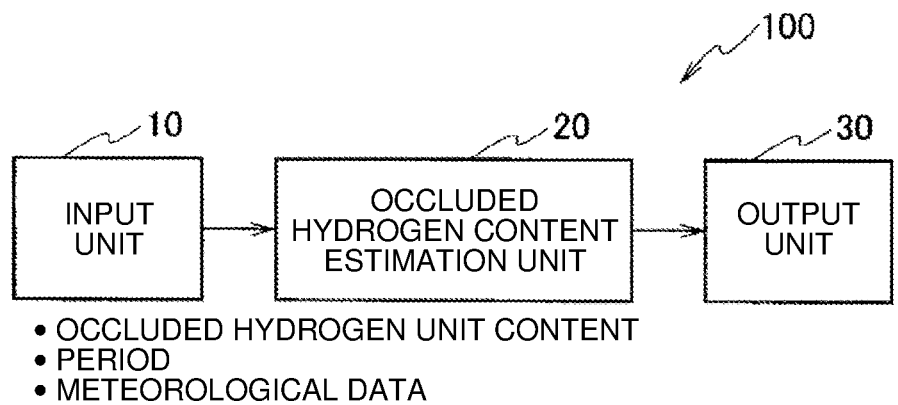
FIG. 1 is a view showing an exemplary functional configuration of an occluded hydrogen content estimation device according to an embodiment of the present invention.

Hereinafter, embodiments of the present invention will be described with reference to the drawings. The same reference characters are given to the same components throughout the drawings, and the description thereof will not be repeated.

Occluded Hydrogen Content Estimation Device

FIG. 1 is a view showing an exemplary functional configuration of an occluded hydrogen content estimation device according to an embodiment of the present invention.

An occluded hydrogen content estimation device 100 shown in FIG. 1 includes an input unit 10, an occluded hydrogen content estimation unit 20, and an output unit 30. The occluded hydrogen content estimation device 100 can be embodied as, for example, a computer including ROM, RAM, CPU, and the like.

The input unit 10 is a keyboard constituting the occluded hydrogen content estimation device 100, for example. An occluded hydrogen unit content, a period, and meteorological data are inputted through operation of the keyboard.

The occluded hydrogen unit content means a content of hydrogen that is occluded in a metal structure (metal) located in a predetermined environment due to a change in humidity of the environment from a wet state to a dry state. Occlusion means that hydrogen generated by corrosion reactions in a metal is absorbed and stored in the metal.

When the environment is in the atmosphere, the wet state is a humidity of 90% or greater, for example. The dry state is a humidity of 10% or less, for example. When the environment is underground, the wet state means that a water content of the soil is 90% or greater and the dry state means that a water content is 10% or less. The wet state and the dry state thus each represent a state of water content in the environment.

Figure 2:
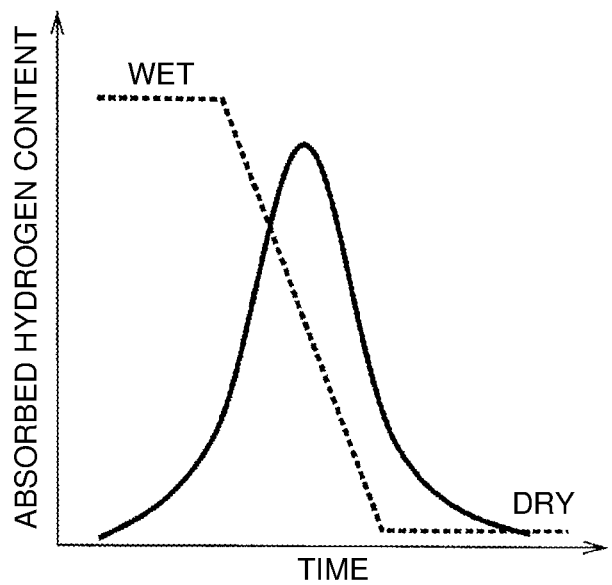
FIG. 2 is a diagram schematically showing a change in content of hydrogen absorbed in a metal when the humidity of the environment where the metal is located changes from a wet state to a dry state.

FIG. 2 is a diagram schematically showing a change in content of hydrogen absorbed in a metal when the humidity of the environment changes from the wet state to the dry state. In FIG. 2, the horizontal axis is time, and the vertical axis is the absorbed hydrogen content.

As shown in FIG. 2, when the water content in the environment changes from the wet state to the dry state, the content of hydrogen absorbed in the metal gradually increases, following the change in the water content, to a maximum value, and then returns to a minimum value. The hydrogen content obtained by integrating the changes in the absorbed hydrogen content is the occluded hydrogen unit content X which is a content of hydrogen stored in the metal through one repetition of the dry and wet states.

The occluded hydrogen unit content X can be measured with a general thermal desorption analyzer and a hydrogen permeation test. The occluded hydrogen unit content X is measured in advance by exposing the same metallic material as that of the target metal structure to the wet state to the dry state. Alternatively, values published in reliable literatures may be employed.

Hydrogen is generated by corrosion reactions and is then absorbed in the metal. Since metal corrosion is caused by repetition of the dry and wet states of the environment, the absorption of hydrogen in the metal also progresses with the repetition of the dry and wet states.

Therefore, the content of occluded hydrogen that is absorbed and stored in the metal can be estimated by multiplying the occluded hydrogen unit content X by the number of repetitions of dry and wet states Y.

Figures 3, 4:
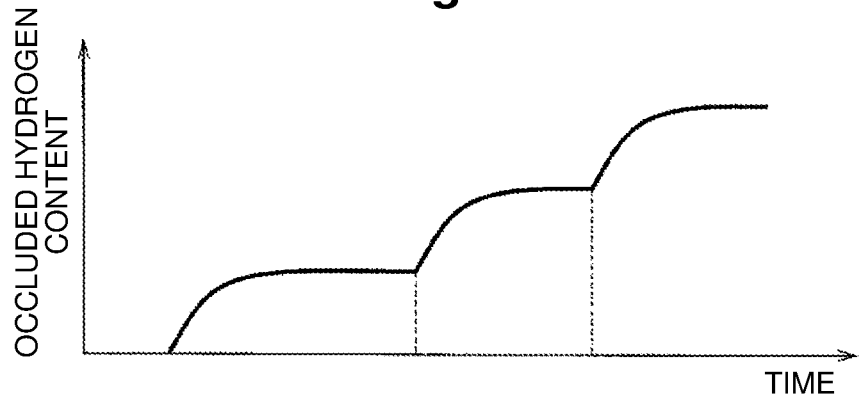
FIG. 3 is a diagram schematically showing a process that the content of occluded hydrogen which is absorbed in the metal increases through repetitions of the dry and wet states.
FIG. 4 is a diagram showing an example of meteorological data of past daily rainfall.

FIG. 3 is a diagram schematically showing a process that the content of occluded hydrogen which is stored in the metal increases with the repetition of the dry and wet states. As shown in FIG. 3, three times repetition of the dry and wet states increases the occluded hydrogen content three times, for example.

The number of repetitions of dry and wet states Y can be determined from, for example, facility information (the age of building) of the metal structure and meteorological data. The meteorological data may be downloaded from the Meteorological Agency's home page.

FIG. 4 shows an example of meteorological data of past daily rainfall downloaded from the Meteorological Agency's home page. The first row shows the date, and the second row shows the area and the rainfall (mm) on each corresponding day. The area in this example is Minato-ku, Tokyo. In this way, the meteorological data can be acquired for each specific area and for each specific period. The rainfalls shown in FIG. 4 are temporary values.

The minimum unit of rainfall is 0.5 mm, and a small rainfall does not lead the water content in the environment to the wet state. Therefore, a day having rainfall of 10 mm or greater is counted as one rainfall, for example. When it rains continuously for straight days, a set of the continuous days is counted as one rainfall.

Figure 5:
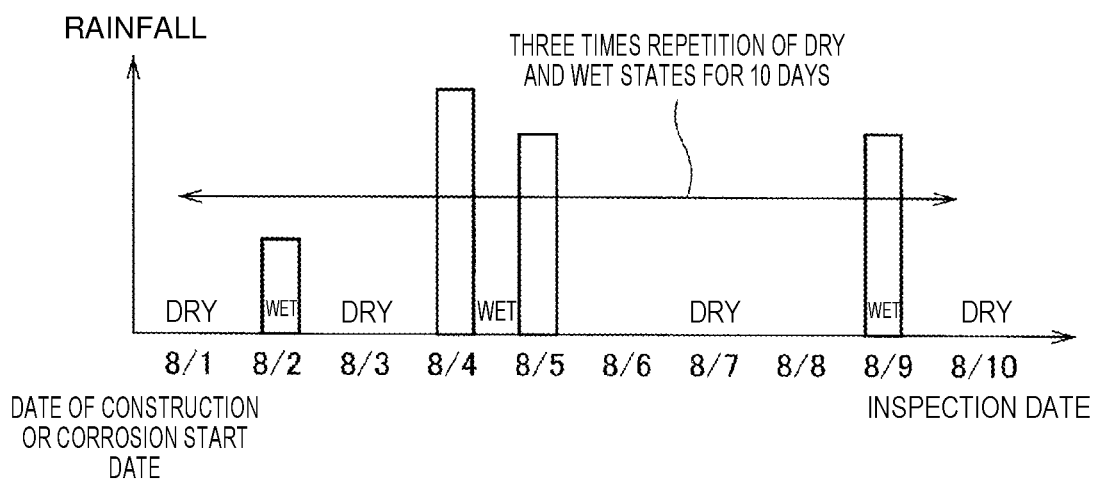
FIG. 5 is a diagram showing another example of meteorological data of rainfall.

FIG. 5 is a diagram showing days having rainfall of 10 mm or greater, with the horizontal axis representing the date. As shown in FIG. 5, three rainfalls are counted between 8/1 and 8/10. The content of occluded hydrogen that is stored in the metal for this period is estimated to X×3.

When the facility information (the age of building) of the metal structure is unknown, the corrosion time can be determined based on corrosion products in the metal structure. The corrosion products are quantitatively analyzed by the powder X-ray analysis method to determine a mass ratio $\alpha/\gamma$ of $\alpha$-FeOOH to $\gamma$-FeOOH, which are iron oxyhydroxides. The mass ratio $\alpha/\gamma$ is known to be correlated with the corrosion time.

Figure 6:
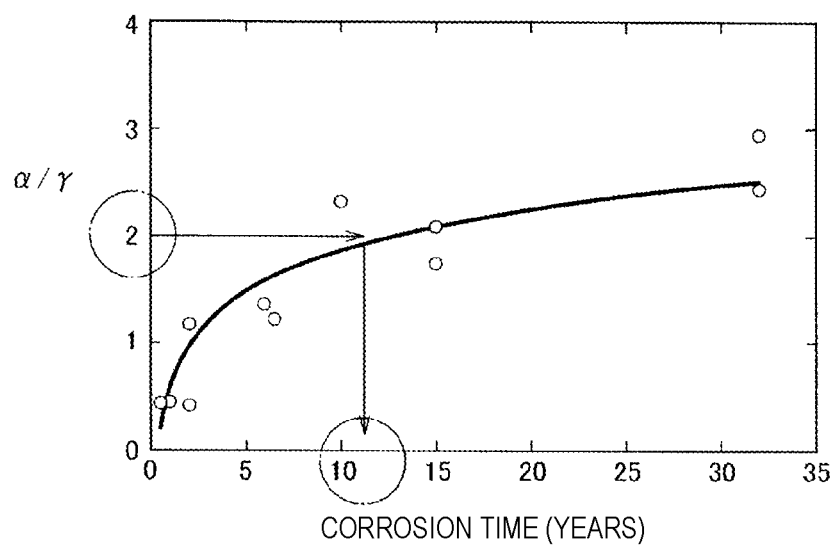
FIG. 6 is a diagram showing a relationship between corrosion time and a mass ratio $\alpha/\gamma$ of corrosion products in the metal.

FIG. 6 is a diagram showing a relationship between the corrosion time and the mass ratio $\alpha/\gamma$. In FIG. 5, the horizontal axis is the corrosion time (years) and the vertical axis is the mass ratio $\alpha/\gamma$.

As shown in FIG. 6, when the mass ratio $\alpha/\gamma$ is known, the corrosion time can be determined. For example, when the mass ratio $\alpha/\gamma=2$, the corrosion time is 11 years. The number of rainfalls (the number of repetitions Y) for the corrosion time of 11 years may be determined as is the case when the facility information of the metal structure is known. That is, the corrosion time corresponds to the age of building of the metal structure.

As described above, the occluded hydrogen content estimation device 100 according to the present embodiment is an occluded hydrogen content estimation device that estimates a content of hydrogen that is occluded in a metal located in a predetermined environment. The occluded hydrogen content estimation device 100 includes the occluded hydrogen content estimation unit 20 that estimates, based on an occluded hydrogen unit content which is a content of hydrogen occluded in the metal due to a change in humidity from a wet state to a dry state, a period after the metal is placed in the predetermined environment, and meteorological data corresponding to the period for an area where the metal is located, a content of occluded hydrogen that is absorbed in the metal for the period. Accordingly, the content of occluded hydrogen that is occluded in the metal structure located in the predetermined environment can be estimated by a simple method using the occluded hydrogen unit content associated with one repetition of the dry and wet states and meteorological data in combination, without destroying and processing the metal structure.

Occluded Hydrogen Content Estimation Method

Figure 7:
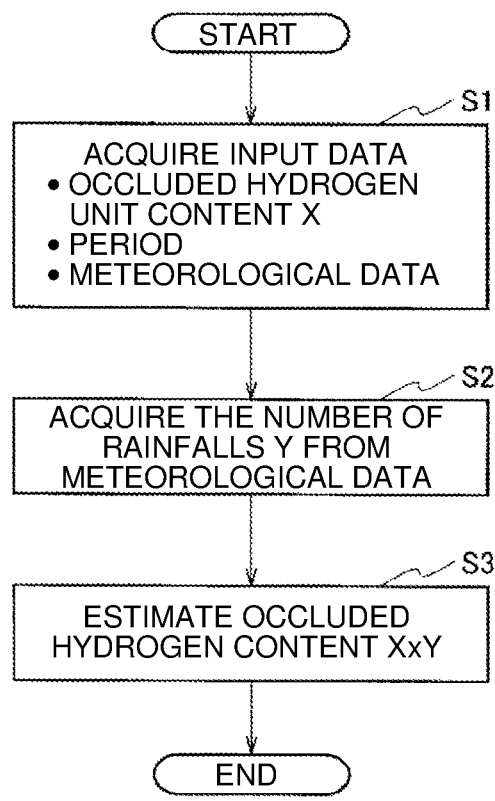
FIG. 7 is a flowchart showing a procedure for the occluded hydrogen content estimation device shown in FIG. 1.

FIG. 7 shows an operation flow of the occluded hydrogen content estimation device 100. As shown in FIG. 7, the operation flow of the occluded hydrogen content estimation device 100 includes an input step S1, an acquisition step S2, and an occluded hydrogen content estimation step S3.

In the input step S1, an occluded hydrogen unit content X, a period, and meteorological data are inputted to, for example, an input port of a computer constituting the occluded hydrogen content estimation device 100. As for the meteorological data, the occluded hydrogen content estimation device 100 may be connected to a server of the Meteorological Agency via a network to acquire the meteorological data in CSV data format from the server and extract necessary data from the CSV data.

In the acquisition step S2, the number of repetitions of dry and wet states Y is acquired from the meteorological data corresponding to the period. The period may be a corrosion time determined based on corrosion products in the metal.

In the occluded hydrogen content estimation step S3, an occluded hydrogen content is estimated by multiplying the occluded hydrogen unit content X by the number of repetitions of dry and wet states Y. The estimated occluded hydrogen content is displayed on, for example, a display constituting the occluded hydrogen content estimation device 100.

As described above, the occluded hydrogen content estimation method according to the present embodiment is an occluded hydrogen content estimation method implemented by the occluded hydrogen content estimation device 100. In the occluded hydrogen content estimation method, the occluded hydrogen content estimation step S3 is performed in which, based on an occluded hydrogen unit content X which is a content of hydrogen occluded in a metal due to a change in humidity from a wet state to a dry state, a period after the metal is placed, and meteorological data corresponding to the period for an area where the metal is located, a content of occluded hydrogen that is absorbed in the metal for the period is estimated.

Figure 8:
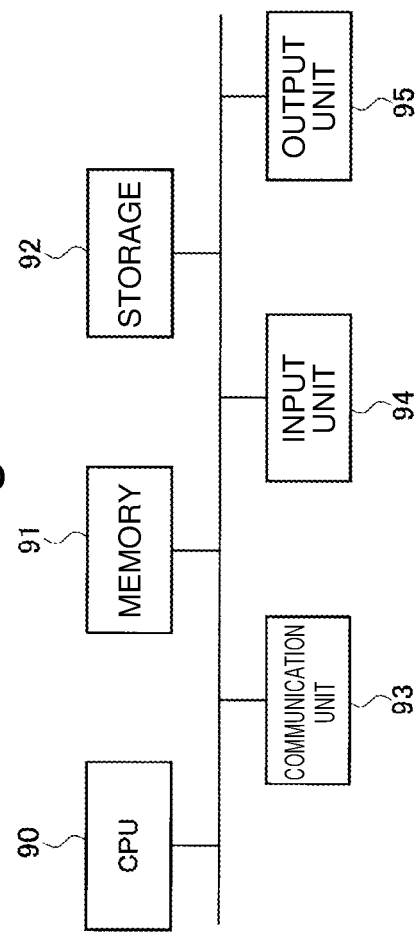
FIG. 8 is a block diagram showing an exemplary configuration of a general-purpose computer system.

The occluded hydrogen content estimation device 100 can be embodied as a general-purpose computer system shown in FIG. 8. For example, in a general-purpose computer system including a CPU 90, a memory 91, a storage 92, a communication unit 93, an input unit 94, and an output unit 95, the function of the occluded hydrogen content estimation device 100 is implemented by the CPU 90 executing a predetermined program loaded in the memory 91. The predetermined program may be stored in a computer-readable recording medium such as HDD, SSD, USB memory, CD-ROM, DVD-ROM, or MO, or may be delivered via a network.

The present invention is not limited to the above embodiments, and can be modified within the scope of the gist thereof. For example, meteorological data may be acquired from the cloud via a network.

As described above, the present invention includes various embodiments which are not described herein as a matter of course. Accordingly, the technical scope of the present invention should be determined only by the matters to define the invention in the scope of claims regarded as appropriate based on the above descriptions.

REFERENCE SIGNS LIST

10 input unit
20 occluded hydrogen content estimation unit
30 output unit
100 occluded hydrogen content estimation device

The invention claimed is:

1. An occluded hydrogen content estimation method implemented by an occluded hydrogen content estimation device, the method comprising:
    estimating a content of hydrogen occluded in a metal due to a change in humidity through at least one repetition of a wet state to a dry state to generate an occluded hydrogen unit content;
    determining a period after a target metal is placed in an area and determining meteorological data corresponding to the period for the area where the metal is located wherein the target metal is a same type is the metal, and
    estimating a content of occluded hydrogen that is absorbed in the target metal for the period based on the occluded hydrogen unit content and the meteorological data corresponding to the period.

2. The occluded hydrogen content estimation method according to claim 1, wherein, in estimating the content of occluded hydrogen that is absorbed in the target metal, the method further comprises multiplying a number of rainfalls in the meteorological data by the occluded hydrogen unit content.

3. An occluded hydrogen content estimation device that estimates a content of hydrogen that is occluded in a target metal located in a predetermined environment, the device comprising:
    an occluded hydrogen content estimation unit that estimates, based on
        an occluded hydrogen unit content which is a content of hydrogen occluded in a metal of a same type as the target metal due to a change in humidity through at least one repetition of a wet state to a dry state,
        a period after the target metal is placed in the predetermined environment, and
        meteorological data corresponding to the period for an area in the predetermined environment where the target metal is located,
    a content of occluded hydrogen that is absorbed in the target metal for the period.

\* \* \* \* \*